(12) United States Patent
Gharib

(10) Patent No.: US 7,491,170 B2
(45) Date of Patent: Feb. 17, 2009

(54) NONINVASIVE METHODS FOR ASSESSING VALVULAR AND VENTRICULAR DYSFUNCTION

(75) Inventor: Morteza Gharib, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 616 days.

(21) Appl. No.: 10/615,884

(22) Filed: Jul. 8, 2003

(65) Prior Publication Data

US 2004/0193035 A1 Sep. 30, 2004

Related U.S. Application Data

(60) Provisional application No. 60/459,074, filed on Mar. 31, 2003.

(51) Int. Cl.
*A61B 8/00* (2006.01)
(52) U.S. Cl. ..................................................... 600/438
(58) Field of Classification Search ......... 600/508–509, 600/513, 438
See application file for complete search history.

(56) References Cited

U.S. PATENT DOCUMENTS 6,149,595 A * 11/2000 Seitz et al. .................. 600/438
6,379,303 B1 4/2002 Seitz et al.
6,517,485 B2 2/2003 Torp et al.

OTHER PUBLICATIONS

Alexandre Ciappina Hueb et al., "Ventricular remodeling and mitral value modifications in dilated cardiomyopathy: new insights from anatomic study", *The Journal of Thoracic and Cardiovascular Surgery*, vol. 124, No. 6, pp. 1216-1224.
Gerald D. Buckberg, "Congestive heart failure: treat the disease, not the symptom—return to normalcy," *The Journal of Thoracic and Cardiovascular Surgery*, vol. 125, No. 3, pp. S41-S49.
Daniel Burkoff, "New heart failure therapy: the *shape* of things to come?", *The Journal of Thoracic and Cardiovascular Surgery*, Mar. 2003, pp. S50-S52.
D. Craig Miller, "Ischemic mitral regurgitation reducx—to repair or to replace?" *The Journal of Thoracic and Cardiovascular Surgery*, Mar. 2003, pp. S58-S61.
M. Gharib et al., "Pulsatile Heart Flow: A Universal Time Scale", *Proceedings of the 2nd International Conference on Experimental Fluid Mechanics*, at Torino, Italy on Jul. 4-8, 1994, pp. 34-39.

* cited by examiner

*Primary Examiner*—George R Evanisko
*Assistant Examiner*—Rex Holmes
(74) *Attorney, Agent, or Firm*—Law Office SC Harris

(57) ABSTRACT

This invention provides a system and a method for monitoring a patient's Formation number (Fn) and comparing the measured Fn to the baseline data of healthy persons population or to the patient's past history data to assess the degree of ventricular and/or valvular dysfunction, wherein the valvular dysfunction may comprise dilated cardiomyopathy, hypertrophic cardiomyopathy, ischemic cardiomyopathy, restrictive cardiomyopathy, or the like.

14 Claims, 4 Drawing Sheets

NONINVASIVE METHODS FOR ASSESSING VALVULAR AND VENTRICULAR DYSFUNCTION

CROSS-REFERENCE TO RELATED APPLICATION

The present application claims the benefit of provisional application Ser. No. 60/459,074, filed Mar. 31, 2003; the entire contents of which are incorporated herein by reference.

FIELD OF THE INVENTION

The present invention generally relates to assessment of heart valve functions of a patient; more particularly, the invention relates to detecting ventricular dysfunctions such as dilated cardiomyopathy through clinically measuring and calculating a dynamic transmitral flow time index known as "Formation number (Fn)" and comparing it with baseline data. The present invention focuses on the dynamic characteristics of early (diastolic) transmitral flow in human and offers a dynamic time index that can be used as a lump index to identify deviations from normality in diastolic cardiac function.

BACKGROUND OF THE INVENTION

The valvular and ventricular dysfunctions affect the quality life of tens of thousands patients. More than 28,000 deaths in 2001 are caused by cardiomyopathy. However, there is little convenient noninvasive assessment approach for quantifying the severity of the valvular dysfunction for the early to moderate stage patients as an aid for later therapeutic management.

The circulatory system consists of a heart and blood vessels. In its path through the heart, the blood encounters four valves. The valve on the right side that separates the right atrium from the right ventricle has three cusps and is called the tricuspid valve. It closes when the ventricle contracts during a phase known as systole and it opens when the ventricle relaxes, a phase known as diastole.

The pulmonary valve separates the right ventricle from the pulmonary artery. It opens during systole, to allow the blood to be pumped toward the lungs, and it closes during diastole to keep the blood from leaking back into the heart from the pulmonary artery. The pulmonary valve has three cusps, each one resembling a crescent and it is also known as a semi-lunar valve.

The mitral valve, so named because of its resemblance to a bishop's mitre, is in the left ventricle and it separates the left atrium from the ventricle. It opens during diastole to allow the blood stored in the atrium to pour into the ventricle, and it closes during systole to prevent blood from leaking back into the atrium. The mitral valve and the tricuspid valve differ significantly in anatomy. The annulus of the mitral valve is somewhat D-shaped whereas the annulus of the tricuspid valve is more nearly circular.

The fourth valve is the aortic valve. It separates the left ventricle from the aorta. It has three semi-lunar cusps and it closely resembles the pulmonary valve. The aortic valve opens during systole allowing a stream of blood to enter the aorta and it closes during diastole to prevent any of the blood from leaking back into the left ventricle.

In a venous circulatory system, a venous valve is to prevent the venous blood from leaking back into the upstream side so that the venous blood can return to the heart and the lungs for blood oxygenating purposes.

The effects of valvular dysfunction vary. Mitral regurgitation has more severe physiological consequences to the patient than does tricuspid valve regurgitation. In patients with valvular insufficiency it is an increasingly common surgical practice to retail the natural valve, and to attempt to correct the defects. Many of the defects are associated with dilation of the valve annulus. This dilatation not only prevents competence of the valve but also results in distortion of the normal shape of the valve orifice or valve leaflets. A suitable approach for treating an annulus, including repair of a valve, valve replacement, implantation of an annuloplasty ring or annulus tissue shrinkage depends on the detection and determination of the severity of the valvular dysfunction.

Cardiomyopathy is a type of heart diseases in which the heart is abnormally enlarged, thickened and/or stiffened. As a result, the heart muscle's ability to pump blood is usually weakened. The condition typically begins in the walls of the heart's lower chambers, and more severe cases may affect the walls of the upper chambers, as well. This damage to the heart walls inhibits the ability of the heart to function effectively, which commonly results in congestive heart failure. Dilated cardiomyopathy (DCM) is a condition in which the heart's ability to pump blood is decreased because the heart's main pumping chamber, the left ventricle, is enlarged and stiff; this causes a decreased ejection fraction (the amount of blood pumped out with each heart beat). In general, it prevents the heart from relaxing and filling with blood as it should. Over time, it can affect the other heart chambers as well.

Hueb and associates studied the behavior of the mitral valve ring and the left ventricle in dilated cardiomyopathy (J Thorac Cardiovasc Surg 2002; 124:1216-24). They reported in ischemic or idiopathic dilated cardiomyopathy, dilation of mitral ring is proportional and does not exclusively affect the posterior portion. The degree of left ventricular dilation does not determine the degree of dilation of the mitral ring because they are independent processes. It is, therefore, one object of the present invention to provide a method for measuring a patient's Formation number (Fn) and comparing the measured Fn to the baseline data of healthy persons to assess the degree of valvular normality or valvular dysfunction Therefore, it is one aspect of the present invention to provide a system and method for assessing the patient's valvular dysfunction due to cardiomyopathy or fibrillation by analyzing the data from noninvasive ultrasound scanning or magnetic resonance imaging.

SUMMARY OF THE INVENTION

In one aspect of the present invention, it is provided a method for assessing valvular dysfunction comprising providing a baseline data of Formation number (Fn) from healthy persons, measuring a patient's Fn, and comparing the measured Fn to the baseline data so as to obtain a differential Fn, wherein the differential Fn is indicative of the valvular dysfunction. The valvular dysfunction is identified from a group consisting of dilated cardiomyopathy (DCM), hypertrophic cardiomyopathy, ischemic cardiomyopathy, restrictive cardiomyopathy, atrial fibrillation, or the like. In one embodiment, the Fn is measured by using a noninvasive procedure selected from a group consisting of ultrasound scanning, MRI (magnetic resonance imaging) scanning, and electromagnetic imaging technique.

In another aspect of the present invention, it is provided a method for assessing progress of valvular dysfunction of a patient comprising providing a baseline data of Formation number (Fn) from the patient, measuring a patient's Fn over time, and comparing the measured Fn to the baseline data so as to obtain a differential Fn, wherein the differential Fn is indicative of the progress of the valvular dysfunction.

In still another aspect of the present invention, it is provided a system for assessing the valvular functions of a patient after a cardiac operation comprising providing a baseline data of Formation number (Fn) from the patient before the operation, measuring a patient's Fn intermittently after the operation, and comparing the measured Fn to the baseline data so as to obtain a differential Fn, wherein the differential Fn is indicative of effectiveness of the operation. In one embodiment, the cardiac operation is selected from a group consisting of valve replacement, annuloplasty ring replacement, valve repair, annular tissue shrinkage, and percutaneous annulus repair.

DETAILED DESCRIPTION OF THE EXEMPLARY EMBODIMENTS

Figure 1:
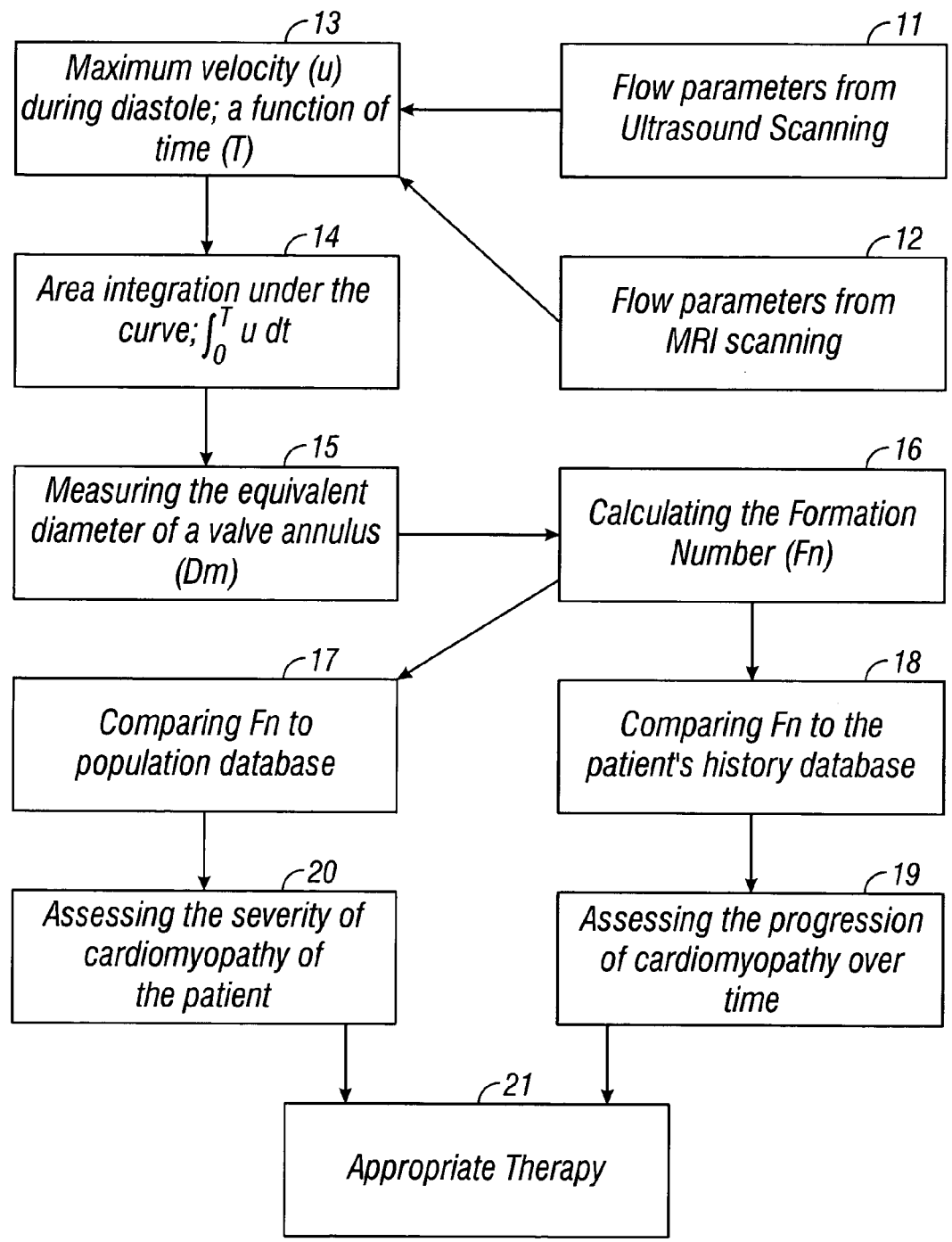
FIG. 1 is a block diagram of steps for measuring a patient's valvular flow parameters.
Figure 2A:
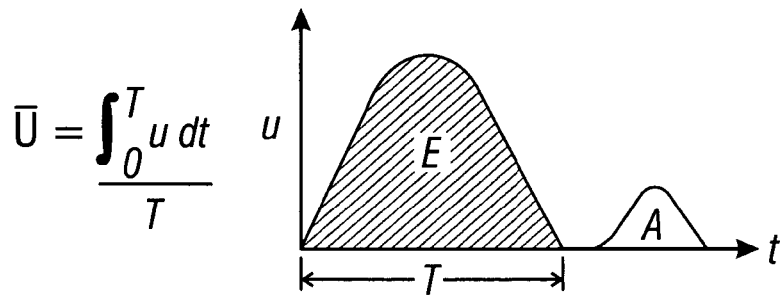
FIG. 2 is the patient's valvular flow parameters used in calculating the Formation number (Fn).
Figure 2B:
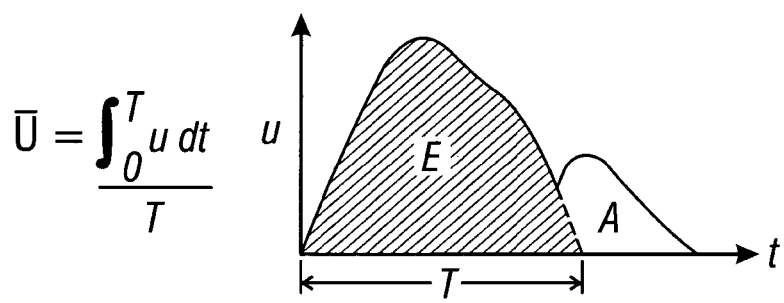
Figure 2C:
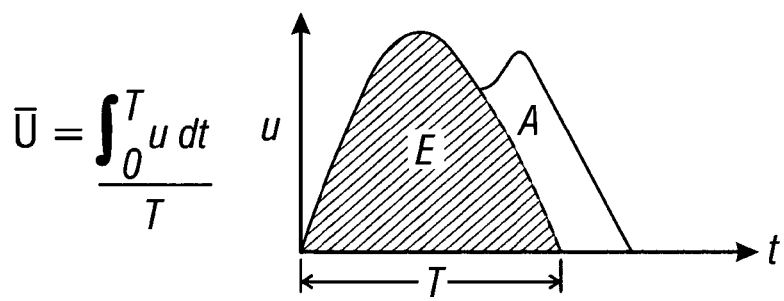
Figure 2D:
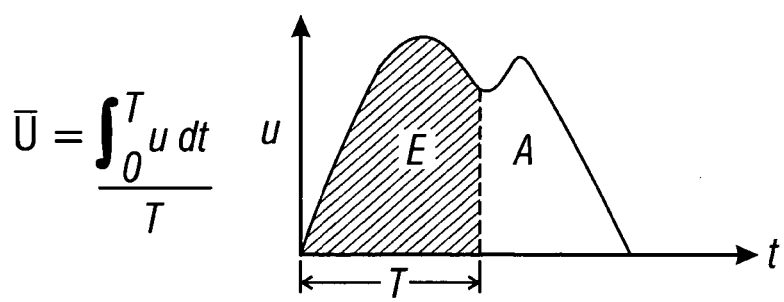

The preferred embodiments of the present invention described below relate particularly to measuring and assessing the Formation number (Fn) of a patient which is indicative of the valvular and ventricular normality or dysfunction through comparing the measured Fn with the population database or against the patient's historic data. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

The Formation Number (Fn)

The maximum efficiency of cardiac filling requires that pressure in the left ventricle drop rapidly and strongly during the early isovolumetric phase of the diastole prior to the opening of mitral valve. The acceleration and maximum velocity attained by the transmitral blood flow from the atrium to the left ventricle depends on the rate and magnitude of the aforementioned pressure-drop in the left ventricle. Thus any index that could characterize the combined effect of blood flow's acceleration and magnitude in normal heart would also reflect the state of ventricular myocardium during isovolumetric and subsequent non-isovolumetric relaxation.

From various ultrasound and MRI studies of the left ventricle, it appears that diseases such as dilated cardiomyopathy would impact blood flow characteristics during early diastolic phase through altering the compliance, stiffness and contractility of the myocardium mass. In this invention, a non-dimensional parameter is proposed by combining average flow during the early filling phase (E-wave) with the duration of E-wave and the diameter of a mitral annulus. Non-dimensional numbers are important analysis and diagnostic tools in the field of fluid mechanics. It is expected that such numbers (parameters) by not having a dimension such as length, time or mass can be used to characterize main fluid dynamic features of certain families of flows. For example, some non-dimensional parameters (e.g., Reynolds numbers) are used to identify low drag laminar flows from high drag turbulent flows.

Two-dimensional, pulsed Doppler echocardiography was performed using commercially available ultrasound machines (Toshiba 140A and Hitachi EUB-165 with 2.5, 3.75, or 5 MHz transducers). Transmitral flows were recorded with the ultrasound transducer paced at the cardiac apex and guided by two-dimensional echocardiographic imaging in a four chamber view. A pulsed Doppler sample volume was placed in the center of the atrio-ventricular junction at the level of the mitral annulus. Once adequate transmitral blood flow velocities had been recorded, velocity time integrals for early diastolic transmitral flow are measured using the track ball systems on the echo systems. The mitral annular diameter (Dm) is also measured at end-diastole using the calibrated track ball measurements from the frozen images. Doppler measurements are averaged over three cardiac beats. Then, the Formation number is calculated using the equation provided below.

Figure 3:
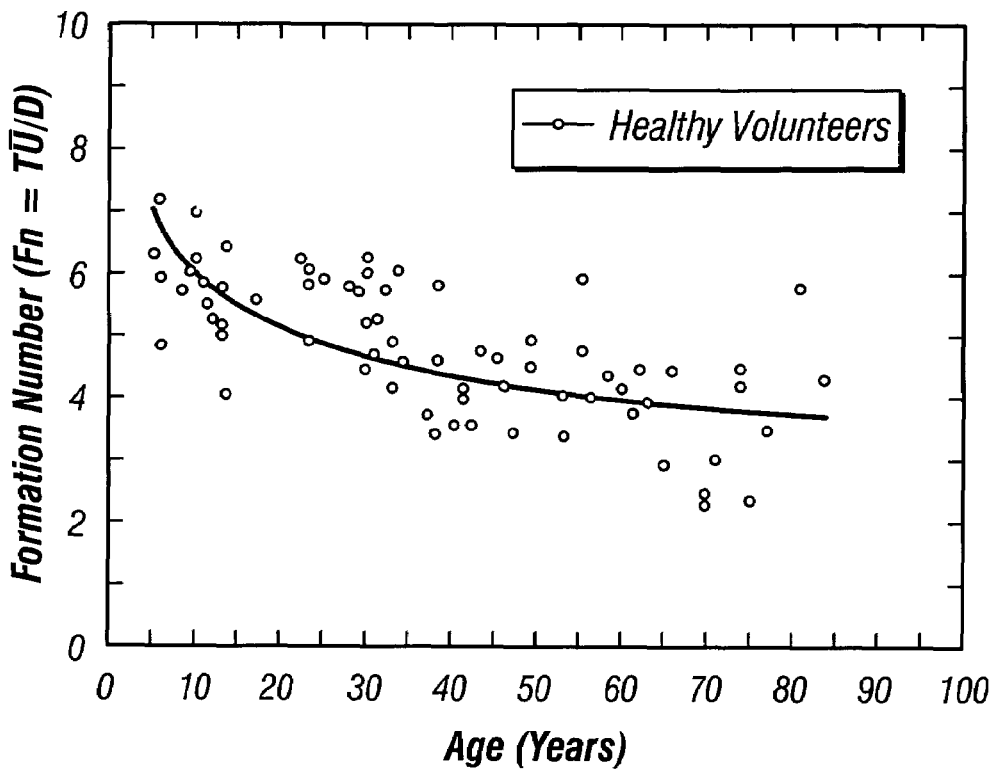
FIG. 3 is an embodiment of the population baseline Formation number as a function of patient's age.

As shown in FIG. 3, the Formation numbers from 73 normal, healthy subjects ranging in age from 5 days to 84 years are compiled. The statistical significance and importance of the narrow range of the Formation number becomes obvious when one considers the broad spectrum of the ages and backgrounds of the test subjects. A low Formation number might indicate poor volume efficiency due to low average velocity, enlarged mitral annulus ring or a short diastolic period, such as in dilated cardiomyopathy. A high value of Formation numbers can be indicative of a high heart rate which results in excessive mean velocities through the heart valve, which may include tachycardias, atrial fibrillation, hypertrophic cardiomyopathy, or the like.

In a preferred embodiment, FIG. 1 shows a schematic block diagram of steps for measuring a patient's valvular flow parameters. In operations, flow parameters (block 13), such as maximum velocity during diastole, which is a function of time, are measured by ultrasound scanning (block 11) or MRI (magnetic resonance imaging) scanning (block 12). The velocity is integrated to yield the average velocity (block 14). The equivalent diameter Dm is measured from the scanning data (block 15). The Formation Number is, thereafter, calculated from the measured parameters (block 16). In one embodiment, the measured Fn is compared to population database (block 17) to assess the severity of the cardiomyopathy of the patient (block 20) or compared to the patient's historic database (block 18) to assess the progression of the patient's cardiomyopathy over time (block 19). In either case, appropriate cardiac therapy may be thereafter prescribed by a physician (block 21).

The Flow parameters comprise the average velocity ($\bar{U}$) during a diastolic period (E-wave), which is a function of elapsed time (t), the major diastolic filling period (T of E-wave), and equivalent diameter of a valve annulus (Dm). The equivalent diameter is defined as the circumference of the annulus divided by $\pi$. In a circular annulus, the equivalent diameter is the annular circle's diameter. The flow parameters may be obtained from noninvasive ultrasound scanning, MRI scanning, or other electromagnetic imaging techniques.

Referring to FIG. 2, several velocity profiles are shown in FIGS. 2(a), 2(b), 2(c) and 2(d). Depending on which technique is employed, a consistent method should be used for the particular patient when comparing the Fn over time. The area under the maximum velocity u is integrated and thereafter, the average velocity ($\bar{U}$) of the filling period (T of E-wave) is obtained by $\bar{U}=\int u\,dt$ integrated from time t=0 to time t=T. The upper limit of T can be defined to improve sensitivity of Fn to certain diastolic dysfunctions. The Formation No. (Fn) is defined as a non-dimensional parameter as follows:

$$Fn = T \times \bar{U}/Dm$$

In one aspect, the measured or calculated Formation number is used to compare with the population database of healthy patients at the specific age of the patient as illustrated in FIG. 3. A power line curve showing the variation of Fn with age is shown in FIG. 3. This curve, as the baseline data of Formation number (Fn) from healthy persons, shows a steady decrease of Fn in the early stages until it reaches a baseline value of 4.5 for the ages over 30. The mean Formation number for the whole data set is about 4.8. The Formation Number of a cardiac-healthy person should essentially fall on or within a non-statistically significant variations range from the Fn curve in FIG. 3.

Figure 4:
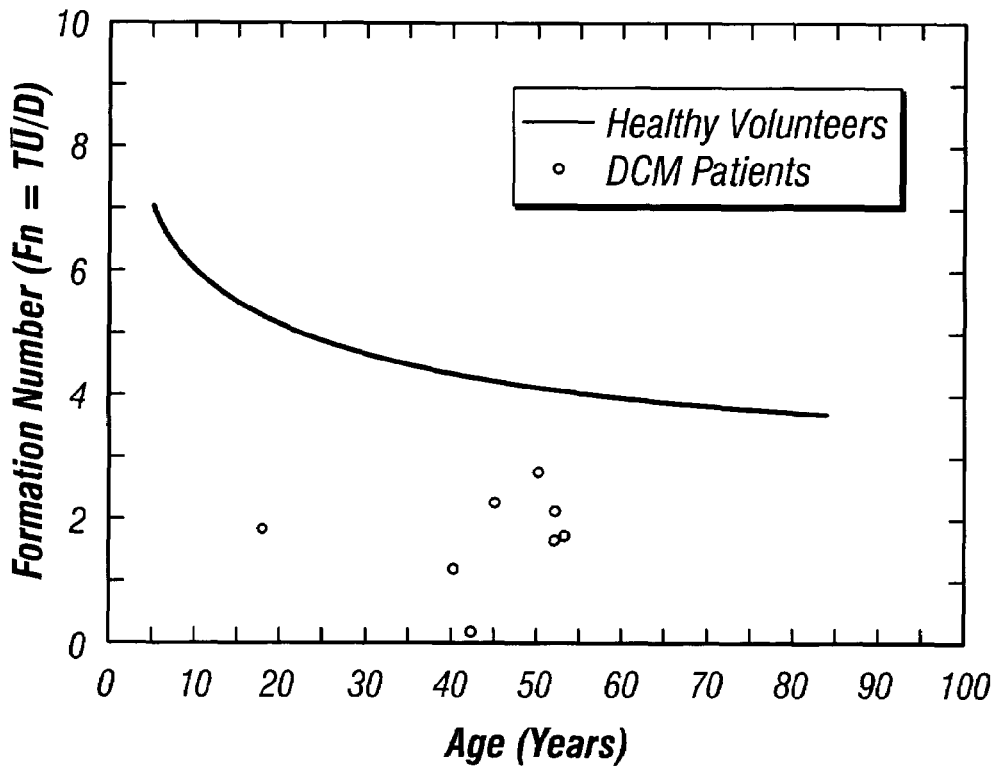
FIG. 4 is an embodiment of the Formation number of DCM patients as compared to the population baseline Fn.

For illustration, FIG. 4 shows a marked decrease in the Formation number for the patients with dilated cardiomyopathy (DCM). For example, a patient with a Formation number of 1.3 at an age of 40 (against a normal baseline data of 4.4 from FIG. 3) is indicative of significant ventricular and/or valvular dysfunction, such as dilated cardiomyopathy. In some aspect of the present invention, it is provided a method for assessing valvular dysfunction comprising providing a baseline data of Formation number (Fn) from healthy persons, measuring a patient's Fn, and comparing the measured Fn to the baseline data so as to obtain a differential Fn, wherein the differential Fn is indicative of the valvular dysfunction. The significance of the differential Fn and the degree of the differential Fn serves as a diagnostic tool for physicians in cardiac management and follow-up therapy.

Figure 5:
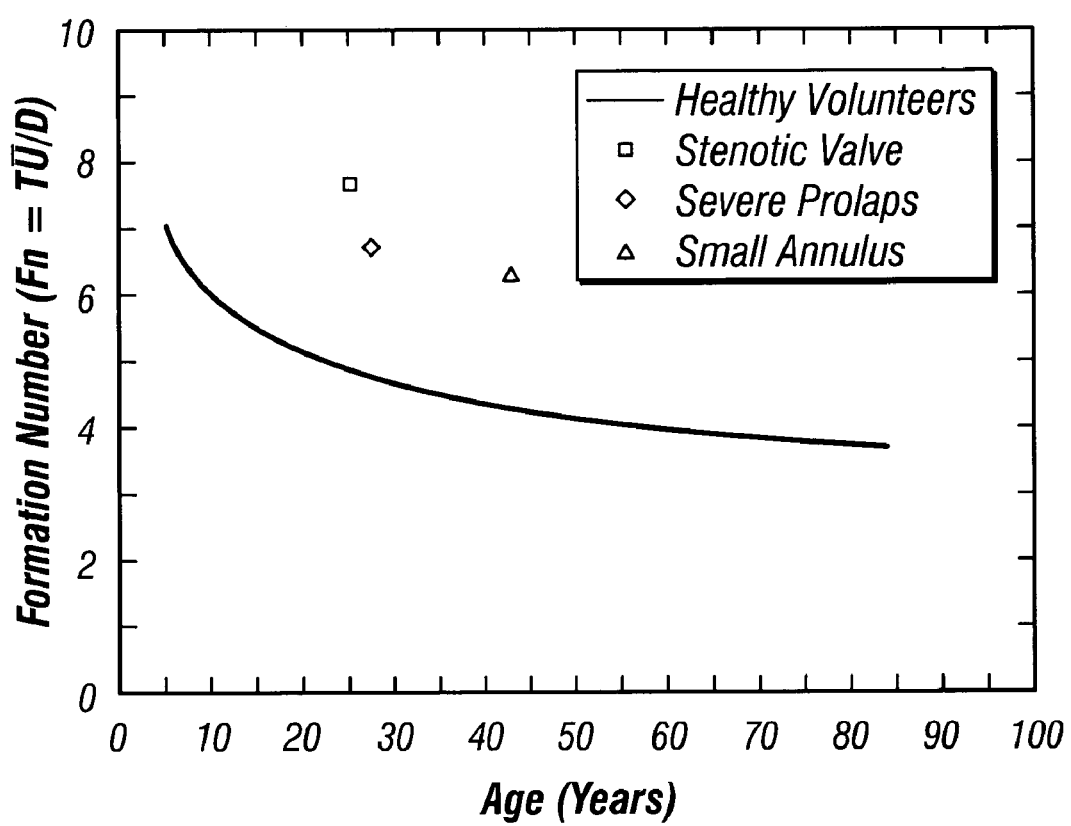
FIG. 5 is an embodiment of the Formation number of stenotic valve patients as compared to the population baseline Fn.

For another illustration, FIG. 5 shows an embodiment of the Formation number of stenotic valve patients as compared to the baseline data of Formation number (Fn) from healthy persons (the power line curve from FIG. 3). The Formation Number for cardiomyopathy patients is generally lower than that of a healthy patient population. On the contrary, the patients with stenotic valve, severe prolaps or small annulus tend to have their Formation Number higher than that of healthy volunteers population.

In another aspect, the measured or calculated Fn is used to compare with the same patient's historical data. For example, the same patient with a Formation number of 2 at age of 50 is indicative of significant worsening of valvular dysfunction when compared to the Fn of 3 at an early age of 40. By following the general curvature of the power line from FIG. 3, it could predict the Fn at a later age for that same patient. Appropriate therapy should have been done on this patient. Therefore, it is one object of the present invention to provide a system, method, and noninvasive apparatus for assessing the patient's valvular dysfunction due to cardiomyopathy, fibrillation or other unknown reasons by analyzing the data obtained from noninvasive ultrasound scanning or magnetic resonance imaging. In some aspect of the present invention, it is provided a method for assessing progress of valvular dysfunction of a patient comprising providing a baseline data of Formation number (Fn) from the patient, measuring a patient's Fn over time, and comparing the measured Fn to the baseline data so as to obtain a differential Fn, wherein the differential Fn is indicative of the progress of the valvular dysfunction.

In still another aspect of the present invention, it is provided a system for assessing the valvular functions of a patient after a cardiac operation comprising: (a) providing a baseline data of Formation number (Fn) from the patient before the operation; (b) measuring a patient's Fn intermittently after the operation; and (c) comparing the measured Fn to the baseline data so as to obtain a differential Fn, wherein the differential Fn is indicative of effectiveness of the cardiac operation. In one embodiment, the cardiac operation is selected from a group consisting of valve replacement, annuloplasty ring replacement, valve repair, annular tissue shrinkage, percutaneous annulus repair and the like.

Although preferred embodiments of the invention have been described in detail, certain variations and modifications will be apparent to those skilled in the art, including embodiments that do not provide all of the features and benefits described herein. Accordingly, the scope of the present invention is not to be limited by the illustrations or the foregoing descriptions thereof.

What is claimed is:

1. A method for assessing progress of valvular dysfunction of a patient comprising:
    determining flow parameters of a patient's valve using non-invasive techniques, said flow parameters consisting of an amount of flow over time in an annulus, a diastolic filling period and information indicative of a size of said annulus;
    using only said flow parameters to determine a Formation number indicative of cardiac information including information about said annulus, where said Formation number is a non-dimensional parameter;
    providing a baseline data of Formation number (Fn) from said patient;
    measuring a patient's Fn over time; and
    comparing the measured Fn to said baseline data so as to obtain a differential Fn; and
    using the differential Fn as an assessment of a progress of the valvular dysfunction.

2. The method of claim 1, wherein the valvular dysfunction is selected from a group consisting of dilated cardiomyopathy, hypertrophic cardiomyopathy, ischemic cardiomyopathy, and restrictive cardiomyopathy.

3. The method of claim 1, wherein the valvular dysfunction is atrial fibrillation.

4. The method of claim 1, wherein the Fn is measured by using a noninvasive procedure of ultrasound scanning.

5. The method of claim 1, wherein said determining the Fn uses a noninvasive procedure of MRI (magnetic resonance imaging) scanning.

6. The method of claim 1, wherein said determining the Fn uses a noninvasive procedure of an electromagnetic imaging technique.

7. The method of claim 2, wherein the valvular dysfunction is ventricular dysfunction.

8. A method for assessing the valvular functions of a patient after a cardiac operation comprising:
    determining flow parameters of a patient's heart using non-invasive techniques, said flow parameters consisting of an amount of flow over time in an annulus, a diastolic filling period, and information indicative of a size of said annulus;
    using only said flow parameters to determine a Formation number indicative of cardiac information, where said Formation number is a non-dimensional parameter;
    providing a baseline data of Formation number (Fn) from said patient before said operation;

measuring a patient's Fn intermittently after said operation; and comparing the measured Fn to said baseline data so as to obtain a differential Fn; and using the differential Fn to assess an effectiveness of the operation.

9. The method of claim 8, wherein the cardiac operation is selected from a group consisting of valve replacement, annuloplasty ring replacement, valve repair, annular tissue shrinkage, and percutaneous annulus repair.

10. The method of claim 8, wherein the Fn is measured by using a noninvasive procedure of ultrasound scanning.

11. The method of claim 8, wherein the Fn is measured by using a noninvasive procedure of MRI (magnetic resonance imaging) scanning.

12. The method of claim 8, wherein the Fn is measured by using a noninvasive procedure of an electromagnetic imaging technique.

13. A method as in claim 1, wherein said formation number is a dimensionless number.

14. A method as in claim 8, wherein said formation number is a dimensionless number.

* * * * *